United States Patent
Zhu et al.

(10) Patent No.: US 7,858,375 B2
(45) Date of Patent: Dec. 28, 2010

(54) AIR-STABLE SUPPORTED LIPID BILAYER MEMBRANES

(75) Inventors: Xiaoyang Zhu, North Oaks, MN (US); Yang Deng, Minneapolis, MN (US); Yini Wang, St. Paul, MN (US); David Barriet, St. Anthony, MN (US); Athena Guo, Minneapolis, MN (US)

(73) Assignee: MicroSurfaces, Inc, Austin, TX (US)

( * ) Notice: Subject to any disclaimer, the term of this patent is extended or adjusted under 35 U.S.C. 154(b) by 0 days.

(21) Appl. No.: 12/049,649

(22) Filed: Mar. 17, 2008

(65) Prior Publication Data

US 2008/0241942 A1    Oct. 2, 2008

Related U.S. Application Data

(60) Provisional application No. 60/908,135, filed on Mar. 26, 2007.

(51) Int. Cl.
G01N 33/92 (2006.01)
C40B 40/04 (2006.01)

(52) U.S. Cl. .................. 436/71; 436/174; 427/2.11; 506/15; 506/23; 506/30

(58) Field of Classification Search .................. 436/71, 436/174, 183; 435/7.1, 7.2, 287.1, 287.2; 422/57; 427/2.11; 506/15, 23, 30
See application file for complete search history.

(56) References Cited

U.S. PATENT DOCUMENTS

| | | | | |
|---|---|---|---|---|
| 4,849,343 A * | 7/1989 | Krull et al. | ................... | 205/778 |
| 5,919,576 A * | 7/1999 | Hui et al. | .................... | 428/545 |
| 5,922,594 A * | 7/1999 | Lofås | ...................... | 435/287.1 |
| 6,756,078 B2 * | 6/2004 | Bookbinder et al. | ..... | 427/407.2 |
| 7,132,122 B2 * | 11/2006 | Parikh et al. | ............... | 427/2.13 |
| 2002/0182717 A1* | 12/2002 | Karlsson | .................. | 435/287.2 |
| 2005/0032246 A1* | 2/2005 | Brennan et al. | ............. | 436/518 |

OTHER PUBLICATIONS

Knoll et al. Reviews in Molecular Biotechnology, vol. 74, 2000, pp. 137-158.*
Deng et al. Journal of American Chemical Society, vol. 130, 2008, pp. 6267-6271.*

* cited by examiner

Primary Examiner—Maureen M Wallenhorst (57) ABSTRACT

The present invention relates to methods for fabricating air-stable supported lipid bilayer membranes. In one embodiment, the present invention relates to methods of producing supported lipid bilayer membranes stabilized by sterol groups that are covalently tethered to a solid surface. In a further embodiment, the present invention relates to air-stable supported lipid bilayer membranes produced by the methods of the present invention.

34 Claims, 5 Drawing Sheets

AIR-STABLE SUPPORTED LIPID BILAYER MEMBRANES

CLAIM OF PRIORITY

This application claims priority of U.S. Provisional Application No. 60/908,135, filed Mar. 26, 2007.

FIELD OF INVENTION

The present invention relates to supported lipid bilayer membranes that are both air and fluid stable and find applications in membrane protein microarrays, membrane protein sensors, biocompatible materials, and membrane based analytical platforms.

BACKGROUND OF THE INVENTION

The majority of drugs under development target cell surfaces. Examples include molecules that bind G-protein coupled receptors and ion channels, bivalent monoclonal antibody (mAb) or engineered multivalent mAb fragments that recognize cell surface antigens, and other small molecules or nano-particles that attack disease cells based on multivalent recognition. In view of this cell-centered drug development, there is a growing need of high throughput analytical techniques incorporating the fluidic cell membrane environment. Fluidic supported lipid bilayers (SLBs) constitute a benchmark in studying cell surface processes, providing an analytical platform which mimics the cell membrane environment [PNAS, 1984, 81, 6159-6163; Science, 1996, 271, 43-48; Acc. Chem. Res. 2002, 35, 149-157; Nature, 2005, 437, 656-663]. However, due to instability of the SLB under a variety of sample processing or handling conditions, particularly exposure to air [J. Phys. Chem. B 1999, 103, 2554-2559], developing the SLB into a practical and high-throughput technique has been extremely difficult.

Wagner and Tamm [Biophys. J. 2000, 79, 1400-1414;], Knoll et al. [Rev. Mol. Biotech. 2000, 74, 137-158], Naumann et al. [Biomacromolecules 2002, 3, 27-35], and U.S. Pat. Nos. 5,922,594, 6,756,078, and 7,045,171 teach the art of producing supported lipid bilayer membranes with improved stability by covalently tethering a fraction of lipid molecules in the membrane via spacers to polymer cushions or self-assembled monolayer coated solid substrate surfaces, but these tethered supported lipid bilayers did not show air stability. Several strategies have been attempted to provide air stability to the supported lipid membrane. These include: 1) hybrid bilayer [U.S. Pat. No. 5,919,576; Langmuir, 1999, 15, 5128-5135] or biomimetic membrane [Langmuir 1999, 15, 3866-3874] where a stable lipid monolayer assembles onto an alkanethiol self-assembled monolayer or a hydrophobic polymer brush; 2) polymerized membrane from diacetylene-lipid conjugates [Langmuir, 2003, 19, 1752-1765]; 3) protein protected membrane bilayer [J. Am. Chem. Soc. 2004, 126, 6512-6513]; 4) membrane bilayers containing poly(ethyleneglycol) (PEG) conjugated lipids [Langmuir 2005, 21, 7476-7482.]; and 5) trehalose protected membrane bilayers [J. Am. Chem. Soc. 2007, 129, 10567-10574.]. The membrane from approach 1) does not allow the incorporation of transmembrane proteins and thus has limited use. The membrane from approach 2) lacks the lipid mobility necessary for mimicking cell surface functions. The surfaces of membrane bilayers from approaches 3) & 4) are covered with a layer of protecting protein molecules or PEG brushes that may prevent proper interaction of membrane receptors with their targets. In approach 5), which is adapted from anhydrobiotic organisms [Nature Biotech. 2000, 18, 145-146], the supported lipid bilayer becomes air-stable if the solution in contact with the supported lipid bilayer before drying contains a relatively high concentration of trehalose. This approach requires the introduction of a large amount of trehalose into the solution every time the supported lipid bilayer is exposed to air and is not practical in bioanalysis.

Fang et al. teach the art of fabricating air-stable membrane protein microarrays on polar or reactive surfaces, particular γ-aminopropylsilane (GAPS) coated glass surfaces [US 2004/0096914 A1; J. Am. Chem. Soc. 2002, 124, 2394-2395], while McBee and Saavedra reported that SUVs deposited on the GAPS surface did not form SLBs and did not possess sufficient stability upon withdrawing of the sample from the air-water interface [Langmuir 2005, 21, 3396-3399]. The approach of Fang et al. was based on immobilizing protein molecules in membrane fractions. A similar approach was demonstrated by Giess et al. in the so-called "protein-tethered lipid bilayer" [Biophys. J. 2004, 87, 3213-3220]. A disadvantage of these approaches based on immobilized proteins is the lack of protein mobility within the supported membrane. Protein mobility is essential to many cell membrane processes. An excellent example is the interaction of integrin receptors with adhesion proteins at the extracellular matrix (ECM). Binding of integrin receptors to Arg-Gly-Asp (RGD) moiety on ECM proteins triggers not only conformational change in the integrin receptor, but also receptor clustering and dynamic increase in the valency of cell adhesion, a process termed "adhesion strengthening" [Curr. Opin. Cell. Biol. 2003, 15, 547-56; Science 1992, 255, 1671-1677.]. Another example is the immune system, which distinguishes "self" from "non-self" based on the dynamic and multivalent recognition by T-lymphocytes of specific antigenic peptides displayed by the major histocompatibility complex (MHC) on the surface of antigen-presenting cells [Science, 1999, 285, 221-227]. Immobilizing protein molecules may also lead to the loss of protein activity, as demonstrated by Cha et al. [Proteomics, 2005, 5, 416-419].

It is apparent that there is a need for improved methods to produce supported lipid bilayer membranes with the following properties: (i) air-stable; (ii) possessing a high level of fluidity which allows receptor or ligand clustering; (iii) free from obstructions to membrane surface interactions; and (iv) easily implemented in an array format. The present invention utilizes tethered sterols groups incorporated into the bottom leaflet of the supported lipid bilayer membrane to impart the properties listed above. Sterols, particularly cholesterol, are predominant and naturally occurring components of plasma membranes of mammalian and eukaryotes cells. The presence of cholesterol increases the stability and rigidity of liposomes by increasing their area-expansion modulus and bending energies [Biophys. J. 2006, 90, 1639-1649]. The rigid and flat cholesterol molecule imposes conformational ordering locally and increases the packing density of lipid molecules in the immediate surrounding [Annu. Rev. Biophys. Biomol. Struct. 2004, 33, 269-295]. In nature, cholesterol molecules in the cell membrane are known to cluster and phase separate into cholesterol rich and cholesterol deficient domains. These cholesterol clusters only stabilize surrounding lipids in the cholesterol rich domains, but not cholesterol deficient domains. To avoid phase separation in a supported lipid bilayer and to fully take advantage of the stabilizing effect, we immobilize cholesterol groups (also referred to as cholesteryl groups) on a solid support; the immobilized and dispersed cholesterol groups interact with the entire bottom leaflet of a supported lipid bilayer, thus imparting the desired property of air-stability. Air-stability was not achieved in previous studies of supported lipid bilayers on tethered cholesteryl groups in binary thiol self-assembled monolayers (SAMs) on gold surfaces [Langmuir 1998, 14, 839-844] where the mobility of the thiolate anchor and the extensive phase separation in the self-assembled monolayer resulted in domains of cholesteryl thiol separated from those of short hydrophilic thiols [Sensors & Actuators B 2007, 124, 501-509]. Vesicle deposition on such a phase separated surface led to lipid monolayers on the cholesteryl domains while lipid bilayers formed on the hydrophilic thiol domains, without achieving air-stability.

SUMMARY OF THE INVENTION

The present invention relates to methods for fabricating air-stable supported lipid bilayer membranes that maintain lipid mobility.

In one embodiment, the present invention relates to a method of producing air-stable supported lipid bilayer membranes via the following steps: (i) providing a solid surface; (ii) covalently attaching sterol groups to the solid surface; (iii) contacting the sterol functionalized solid surface with a lipid solution.

In a further embodiment, the present invention relates to a method of producing air-stable supported lipid bilayer membranes via the following steps: (i) providing a solid surface coated with a molecular film (polymer cushion, molecular monolayer, or hydrogel); (ii) covalently attaching sterol groups to the molecular film; (iii) contacting the sterol functionalized molecular film with a lipid solution.

In yet another embodiment, the present invention relates to a method of producing air-stable supported lipid bilayer membranes via the following steps: (i) covalently attaching sterol groups to a hydrophilic polymer tether with an end functional group of "A"; (ii) mixing the polymer-tethered sterols with a lipid solution; (iii) providing a solid surface functionalized with a chemical group "B" reactive towards "A" for covalent bond formation; and (iv) contacting the mixed lipid solution from step (ii) with the functionalized surface from step (iii) to form the air-stable supported lipid bilayer membrane.

In yet another embodiment, the present invention relates to the air-stable supported lipid bilayer membranes produced by the methods of the present invention.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DESCRIPTION OF THE DRAWINGS

FIG. 1 is a schematic illustration of one embodiment of the methods of the invention. Step (i) provides a solid support 1 coated with a molecular film 2 (hydrophilic polymer cushion or immobilized molecular monolayer). In step (ii), sterol groups 3 are covalently linked via tethers 4 to the molecular film to produce surface 5: a molecular film coated solid support with surface sterol groups. In step (iii), surface 5 is brought into contact with lipid solution 6 to produce the air-stable supported bilayer lipid membrane 7.

FIG. 2 is a schematic illustration of another embodiment of the methods of the invention. In step (i), the sterol molecule 1 is linked to a molecular tether 2 to produce a tethered-sterol 3 with a terminal group A. In step (ii), the tethered sterol 3 is mixed with a lipid solution containing lipid vesicles (also called liposomes) 4 to produce a membrane solution containing sterol incorporated lipid vesicles 5. Step (iii) provides a solid surface 6 which is coated with a molecular film and functionalized with a chemical group "B" reactive towards "A" for covalent bond formation. In step (iv), the functionalized surface 6 is brought into contact with the mixed lipid solution to form the air-stable supported lipid bilayer membrane 7.

DETAILED DESCRIPTION

The present invention relates to methods for fabricating air-stable supported lipid bilayer membranes on the surface of solid substrates. In one embodiment, the present invention relates to methods of producing supported lipid bilayer membranes stabilized by sterol groups covalently tethered to a solid substrate. In a further embodiment, the present invention relates to air-stable supported lipid bilayer membranes produced by the methods of the present invention.

The supported lipid bilayer membranes produced by the methods of the present invention are air-stable. In this context, "air-stable" means that the supported lipid bilayer membrane remains intact on the substrate surface after the substrate has been removed from the aqueous environment, exposed to the ambient gas environment at room temperature, and re-immersed in aqueous solutions. There is little change to the physical and chemical properties of the supported lipid bilayer membrane after it has been exposed to the ambient gas environment and re-immersed in an aqueous solution. The time duration of exposure to the ambient gas environment can range from a few seconds to a few days.

The supported lipid bilayer membranes produced by the methods of the present invention possess a high level of lipid mobility. In this context, mobility means that lipid molecules within the supported lipid bilayer membrane can freely diffuse and the recovery of fluorescence intensity in a FRAP experiment should be >50% after photobleaching, and more preferably >80% after photobleaching, and most preferably >90% after photobleaching.

Each supported lipid bilayer membrane produced by the methods of the present invention consists of two leaflets: the bottom leaflet contains sterol groups that are covalently attached to the solid substrate surface. The density of the surface tethered sterol groups is preferably between $1\times10^{11}/cm^2$ and $4\times10^{14}/cm^2$, and more preferably between $1\times10^{12}/cm^2$ and $1\times10^{14}/cm^2$, and most preferably between $1\times10^{13}/cm^2$ and $1\times10^{14}/cm^2$. The sterol groups are preferably cholesterols or chemically modified cholesterols. The sterol groups are preferably linked to the solid surface via a molecular tether. Each molecular tether has a length of preferably from about 0.2 nm to about 100 nm, and more preferable from about 0.5 nm to about 5 nm. The supported lipid bilayer membrane produced by the methods of the present invention may contain membrane proteins, peptides, or glycolipids.

The solid substrate can be any solid material, such as glass, silica, metal, metal oxide, ceramics, semiconductor, plastic, or polymer. The substrate surface is preferably covered with a molecular film, such as an immobilized monolayer, and more preferably with a hydrophilic polymer cushion, such as a polyether film or a hydrogel. The surface of the molecular film may optionally contain charged groups, such as —COO$^-$ or —NH$_3^+$, for interaction with zwitterionic or oppositely charged lipid head groups to facilitate the adsorption and rupture of lipid vesicles.

The lipid solution referred to in the present invention is a solution of synthetic or naturally occurring lipids and amphiphilic molecules, such as phospholipids, sphingolipids, ceramides, sterols, etc. The lipid solution may contain vesicles, liposomes, micelles, and monolayer or bilayer membrane fragments. The lipid solution may further contain transmembrane proteins, peripheral membrane proteins, peptides, and glycolipids.

In one embodiment, the present invention relates to a method of producing an air-stable supported lipid bilayer membrane via the following steps: (i) providing a solid substrate surface; (ii) covalently attaching sterol groups to the solid substrate surface; (iii) contacting the sterol functionalized solid surface with a lipid solution. The sterol groups are preferably attached to the solid substrate surface via molecular tethers in step (ii). The lipid solution used in contacting the sterol tethered solid surface preferably contains lipid vesicles or liposomes.

In another embodiment, the present invention relates to a method of producing air-stable supported lipid bilayer membranes via the following steps: (i) covalently attaching sterol groups to a hydrophilic polymer tether with an end functional group of "A"; (ii) mixing the polymer-tethered sterol with a membrane solution; (iii) providing a solid surface functionalized with a chemical group "B" reactive towards "A" for covalent bond formation; and (iv) contacting the mixed lipid solution from step (ii) with the functionalized surface from step (iii) to form the air-stable supported bilayer lipid membrane.

In a further embodiment, the present invention relates to a method of producing air-stable supported lipid bilayer membranes in an array format, e.g., by a robotic spotter.

In yet another embodiment, the present invention relates to the air-stable supported lipid bilayer membranes or membrane arrays produced by the methods of the present invention.

The supported lipid bilayer membranes produced by the methods of the present invention possess the following advantageous properties: 1) they are air-stable; 2) they are highly fluidic; 3) they can be easily produced by deposition of lipid solution on functionalized solid surfaces; 4) they do not require immobilization of protein molecules to the solid surfaces; and 5) they can be implemented in an array format without the need of pre-patterning of the solid surface.

Figure 1:
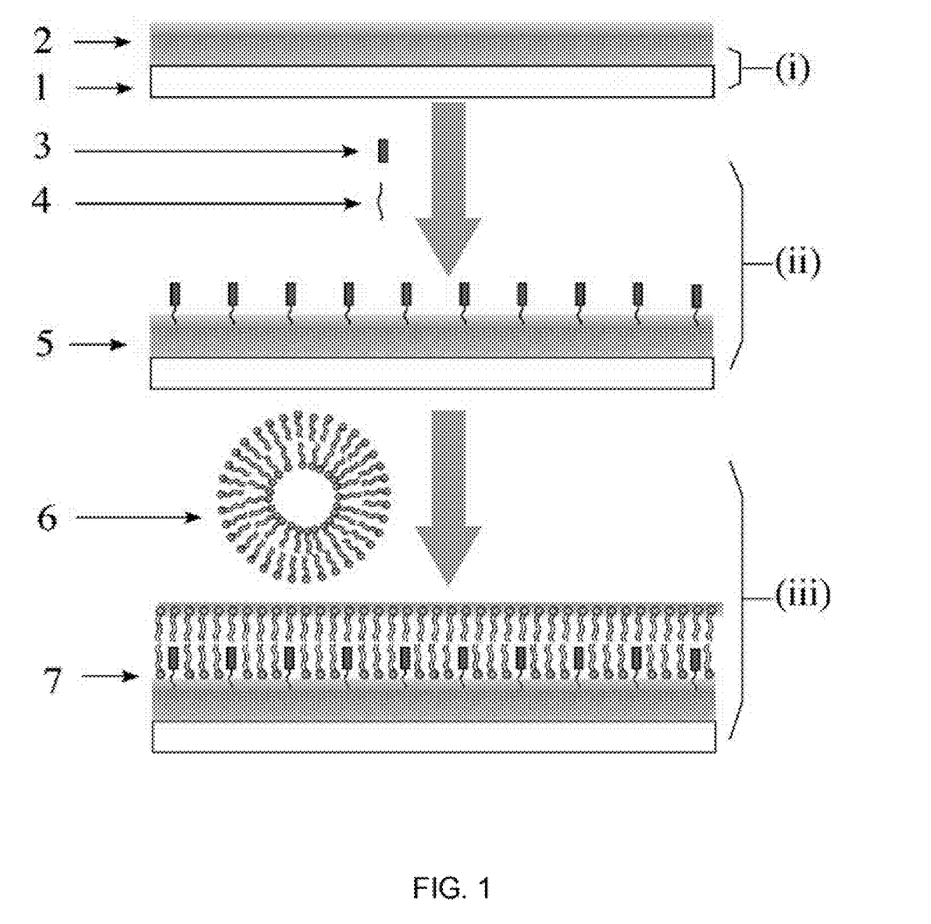
Figure 2:
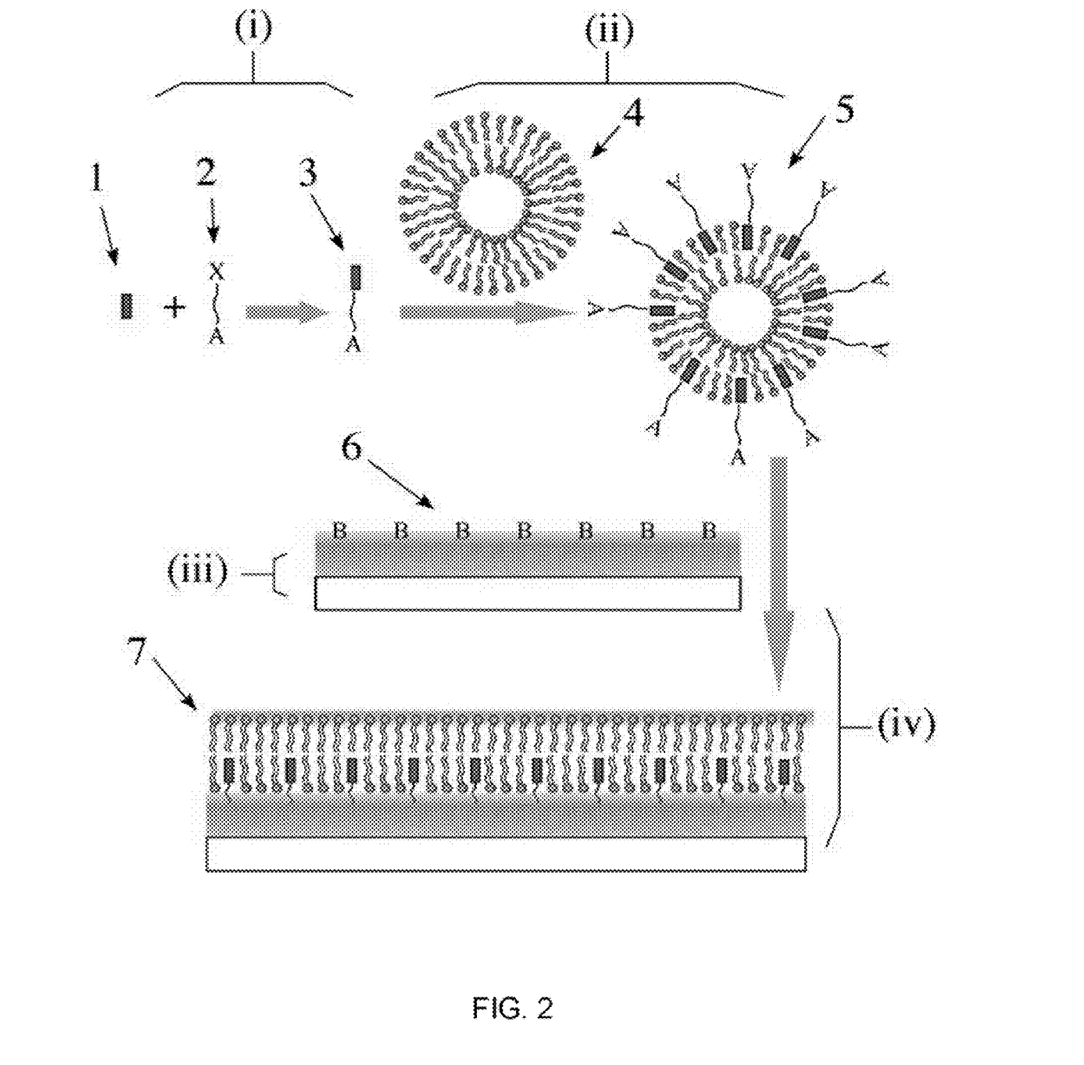
Figure 3:
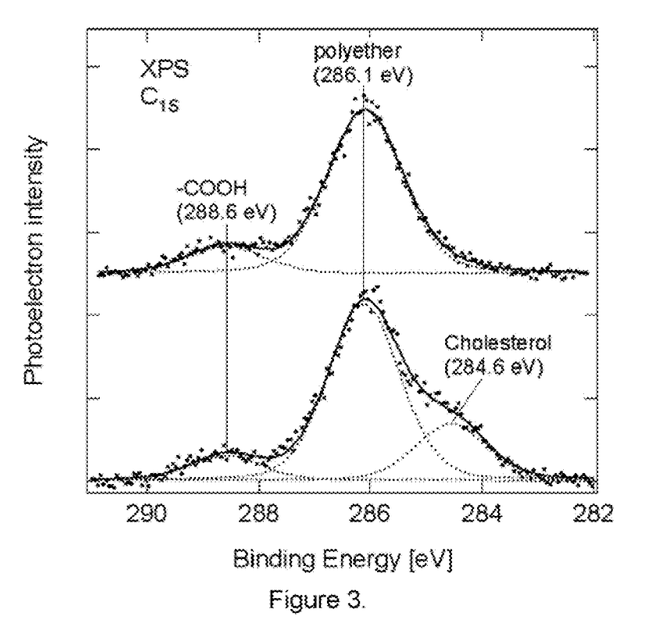
FIG. 3 shows X-ray photoelectron spectra in the C1s region of a polyether surface before (upper) and after (lower) the covalent attachment of cholesterol groups. The peak at an electron binding energy (BE) of 286.1 eV is $C_{1s}$ from the polyether coating. The peak at BE=288.6 eV is $C_{1s}$ from —COOH groups on the polyether surface. The peak at BE=284.6 eV is $C_{1s}$ from cholesterol groups. Quantitative analysis of peak areas gives a surface cholesterol group density of $3.0 \times 10^{13}/cm^2$.

X-ray photoelectron spectroscopy (XPS) was used to characterize the functionalized solid substrate surfaces before the step of contacting a lipid solution (FIG. 3). XPS measurements were carried out on a Perkin-Elmer Phi 5400 spectrometer in an ultrahigh vacuum system. A Mg Kα anode operated at 200 W was used as the source of x-ray radiation at hv=1253.6 eV. An analyzer pass energy of 89.45 eV was used in survey scans and 17.9 eV for high resolution scans.

Fluorescence microscopy and fluorescence recovery after photobleaching (FRAP) were used to characterize the integrity and fluidity of the supported lipid bilayer membrane. All FRAP images were obtained on a Nikon 50i fluorescence microscope. Bleaching was carried out with a 60× objective and a field reducer at full UV excitation power for one minute to give a bleached area diameter of 29 μm. Imaging was carried out with a 20× objective at reduced UV excitation power.

In the following, the invention is illustrated by a non-limiting Example which describes one embodiment of the methods of the present invention.

EXAMPLE

Materials. Egg phosphatidylcholine (EggPC), 1,2-dioleoyl-3-trimethyl ammonium propane (DOTAP), and ganglioside-GM$_1$ were from Avanti Polar Lipids (Alabaster, Ala.). Texas Red tagged dihexadecanoyl-phosphatidylethanolamine (TR-DHPE) was purchased from Invitrogen (Carlsbad, Calif.). The polyether coated glass coverslips were from MicroSurfaces, Inc. (Minneapolis, Minn.). Primary antibodies against PLN (L-15) and pS16-PLN (Ser16) were from Santa Cruz Biotechnology (Santa Cruz, Calif.). FTIC tagged secondary antibody [AffiniPure Donkey Anti-Goat IgG(H+L)] were from Jackson ImmunoResearch Laboratories (West Grove, Pa.). All other chemical reagents were from Sigma-Aldrich (St. Louis, Mo.). Phospholamban (PLN) monomer (C36A, C41F, C46A construct) and pentamer (wild-type) were expressed and purified as previously described [Protein Expr. Purif. 2003, 30, 253-261]. Phosphorylation at S16 (pS16-PLN) was carried out on monomeric PLN as described previously using the catalytic subunit of protein kinase A (Sigma-Aldrich, St. Louis, Mo.) [Biochem. 2005, 44, 4386-4396]. Unlabeled cholera toxin B (CTB) and FTIC dye-tagged CTB were both purchased from Sigma-Aldrich (St. Louis, Mo.).

SUV. Preparation of SUV solution was carried out via the extrusion method of Avanti Polar Lipids. Briefly, mixed lipids were evaporated under argon flow until dry and the lipid mixtures were reconstituted in Tris buffer (50 mM Tris-hydroxymethyl-aminomethane in 100 mM NaCl, pH 7.5) to give a total lipid concentration of 1 mM. Suspension of the lipid mixtures after prefiltration through 0.45 µm pores was forced through a polycarbonate filter with 50 nm pores more than 11 times. This SUV solution was stored at 4° C. until use. To incorporate GM1, we added 2% $GM_1$ (in methanol) to the mixed lipid solution before the drying step. The reconstitution of proteins, monomeric and pentameric phospholamban (PLN), into SUVs has been described elsewhere [Biochem. 2006, 45, 13827-13834]. Briefly, PLN was first dissolved into a 10% SDS solution to give a final protein concentration of ~1 mg/ml. The protein/detergent mixture was then added to the SUV solution (~7 mg/ml) to give a final protein concentration of ~0.2 mg/ml, a lipid:protein (monomer) molar ratio of ~100:1, and a total lipid concentration of ~3.5 mg/ml. The mixture was then subjected to 2-3 days of dialysis using a 10 kDa molecular weight cut-off membrane, until all SDS was removed.

Cholesteryl-polyether Surface. To covalently attach cholesterol groups, we incubated the polyether surface with 30 mM cholesteryl chloroformate in $DMF/CH_2Cl_2$ (1:1) in the presence of a catalytic amount of pyridine at room temperature. The reaction time was varied between 0.5 and 5 hours to give different surface cholesteryl density, which was quantitatively determined for each surface by X-ray photoelectron spectroscopy based on the $C_{1s}$ peak areas.

SLBs. A sufficient amount of the SUV solution was placed on each functionalized surface of interest and incubated for one hour at room temperature. Excess vesicles were removed from the surface by flushing with copious amounts of Tris buffer. To test air-stability, we removed the SLB-covered surface from the buffer solution and left it to dry in air for ~two hours. We rehydrated each surface by placing it back in the buffer solution. Note that all SLB covered surfaces were handled horizontally to avoid excessive shear force from liquid fronts running across the surface. Most washing/rinsing steps were carried out with the SLB covered surfaces facing up at the bottom of Petri dishes and with buffer solutions added and withdrawn at localizations away from the sample surfaces.

Arraying & Immunostaining: SUV solutions were deposited on cholesteryl-polyether surfaces with a robotic arrayer (Molecular Dynamics). To avoid rapid drying of the nanoliter droplet, we added 10% glycerol to each SUV solution. We incubated the arrayed coverslips in high humidity environment for 30 min-1 hour and then rinsed each sample with Tris buffer to remove excess lipids on the surface. For CTB incubation, the sample was incubated with diluted CTB solution (1 nM) for 3 hours. For immunostaining, we incubated the coverslips with primary antibody (1:200 dilution in TRIS buffer) for two hours, followed by sufficient washing and then incubation with secondary antibody solution (1:200 dilution in TRIS buffer) for one hour. We washed each sample with copious amounts of buffer before imaging.

Figure 4:
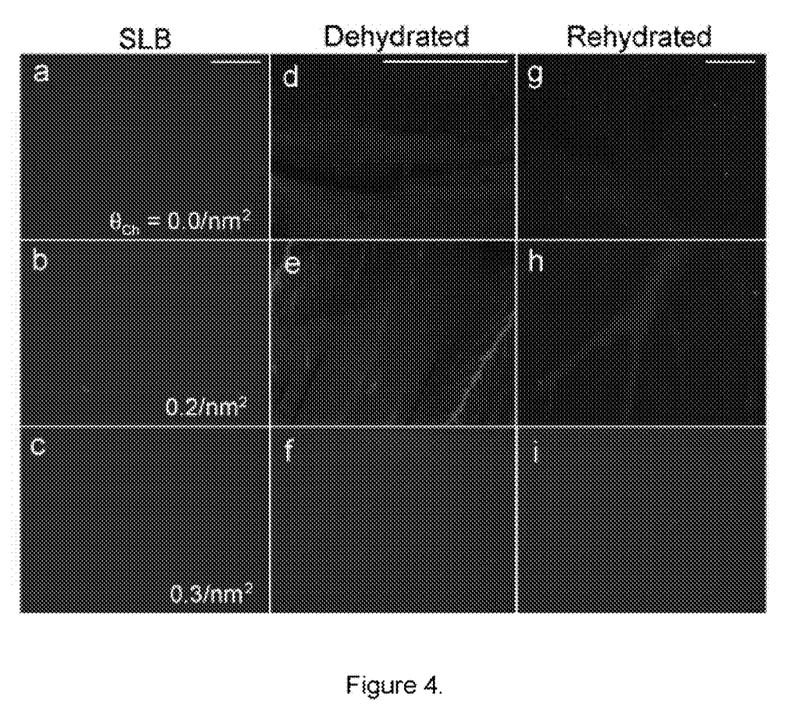
FIG. 4 shows fluorescence microscopy images of supported lipid bilayers formed on a polyether surface with the indicated densities of surface tethered cholesterol groups: $\theta_{Ch}$=0.0 (a, d, g), $2.0 \times 10^{13}$ (b, e, h), and $3.0 \times 10^{13}/cm^2$ (c, f, i). The scale bar (400 μm) for each column is shown at the top. The SLBs are formed from the fusion of SUVs containing 0.5% Texas-Red 1,2-di-hexadecanoyl-sn-glycero-3-phosphoethanolamine (TR-DHPE), 50% egg phophatidylcholine (EggPC), and 50% 1,2-dioleoyl-3-trimethyl ammonium propane (DOTAP). Images for the as-formed SLBs in buffer solution (a, b, c) and those after dehydration (g, h, i) are taken with 4× objective, while those in the dehydrated state (d, e, f) are taken with 10× objective to reveal more details

The fluorescence microscopy images in FIG. 4 are from SLBs formed on surfaces with cholesteryl densities of $\theta_{Ch}=0.0$, $2\times10^{13}$, and $3\times10^{13}/cm^2$, respectively. While SLBs with spatially uniform fluorescence intensity distributions are formed on all surfaces in buffer solutions (a-c), the influence of cholesteryl becomes apparent when the SLB is exposed to air and dehydrated. On surfaces with low cholesteryl densities ($\theta_{Ch}<3\times10^{13}/cm^2$), moving through the water-air interface and drying in air results in desorption and extensive restructuring of surface adsorbed lipid molecules, as evidenced by the lower and non-uniform fluorescence intensity of images (d, e). Upon rehydration of these dried surfaces in buffer solution, most lipid molecules are washed off the surfaces (g, h). In contrast, when the surface cholesteryl density reaches a critical value of $\theta_{Ch}=0.3/nm^2$, fluorescence images of the SLBs remain spatially uniform upon drying (f) and rehydration (i); thus establishing air-stability. Results for $\theta_{Ch}=5\times10^{13}/cm^2$ (data not shown) are similar to those of $\theta_{Ch}=3\times10^{13}/cm^2$.

Figure 5:
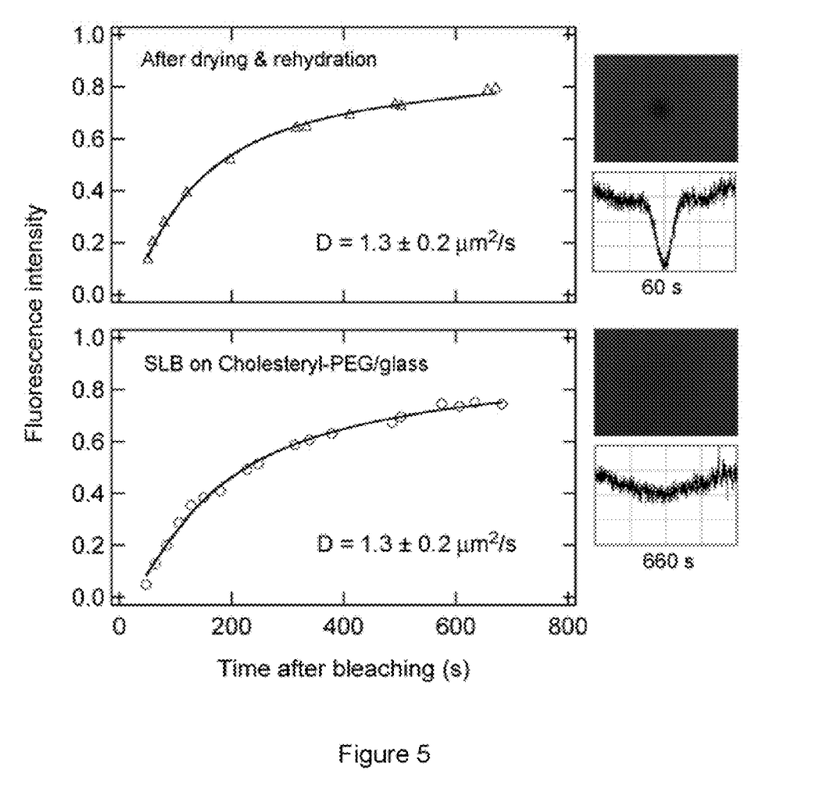
FIG. 5 shows fluorescence-recovery-after-photobleaching (FRAP) results for an SLB formed on a polyether/glass surface with a tethered cholesterol group density of $3.0 \times 10^{13}/cm^2$. The lower panel is for the as-formed SLB and upper panel for the SLB after air-drying and rehydration. The diffusion constants are obtained from fits (solid lines) to the FRAP data and average values from repeated measurements are shown. The fitting function can be found in Axelrod et al. [Biophys. J. 1976, 16, 1055-1069]. The right shows two fluorescence images (240 μm×400 μm) and cross sectional profiles for the rehydrated SLB taken at 60 s and 660 s after photobleaching.

Within the air-stable SLB, lipids remain mobile even after the membrane has gone through dehydration and rehydration, as shown by fluorescence-recovery-after-photobleaching (FRAP) in FIG. 5. Sample fluorescence microscopy images (along with cross-sectional profiles) for the rehydrated SLB are shown on the right side. Similar images are obtained for the as-prepared SLB in buffer solution before drying (not shown). Fitting the FRAP data in FIG. 5 gives lipid diffusion constants of $D=1.3\pm0.2$ $\mu m^2/s$ and total recovery percentage >90% at long times, both before and after the dehydration-rehydration cycle. This diffusion constant is typical for tethered lipid bilayers [Rev. Mol. Biotech. 2000, 74, 137-158].

Figure 6:
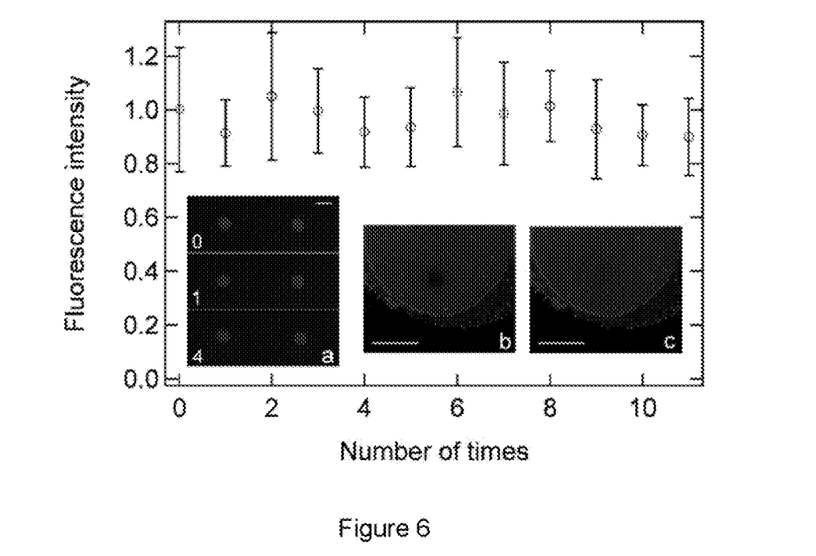
FIG. 6 shows Fluorescence microscope images of a 2×1 array of SLBs on the cholestery-polyether/glass surface ($\theta_{Ch}$=$3.0 \times 10^{13}/cm^2$). The as-formed array is shown at the top and those after air-exposure once and four times are in the middle and bottom, respectively. The data points are fluorescence intensity as a function of the number of times of air-exposure. The zoomed-in images are for a single spot (transferred through the air-water interface once after arraying and washing) taken at (b) 47 s and (c) 600 s after photobleaching. All fluorescence measurements were carried out with the sample in buffer solution. The scale bar is 400 μm in (a) and μm in (b) or (c).

The success in achieving air-stability has enabled us to directly form SLB microarrays simply from robotic spotting. Drying of the nanoliter droplets after arraying is not a problem because of the air-stability of the SLB and because excess lipids are easily washed off. FIG. 6a shows fluorescence images of a 2×1 array of SLB formed from robotic spotting of SUV solution on the cholesteryl-PEG surface and the same array after it has been withdrawn from the air-water interface once and four times, respectively. Insets (b) and (c) show zoomed-in images on one spot taken at 47 s and 600 s, respectively, after photobleaching. Lipid molecules in the SLB spot are clearly in the fluidic state; fitting the FRAP data (not shown) gives similar diffusion constants as those in FIG. 5. The data points in FIG. 6 show that the spot intensity remains constant after the array has been withdrawn from the air-water interface for as many as 11 times, indicating remarkable robustness of the SLB spots.

Figure 7:
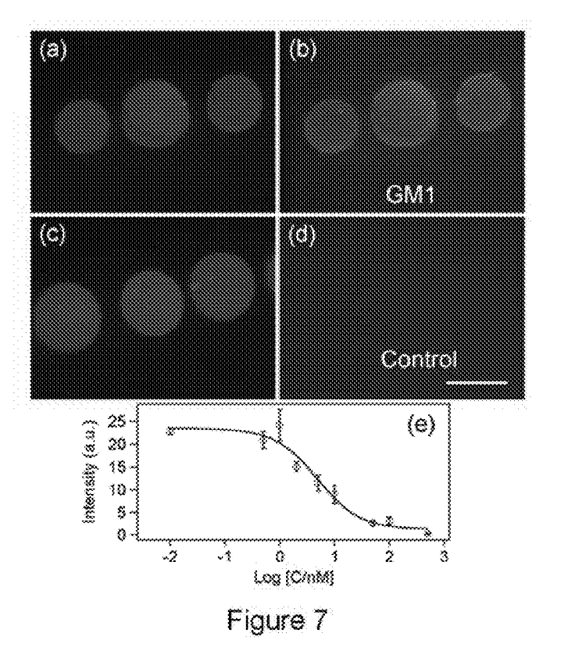
FIG. 7 shows fluorescence microscopic images of SLB arrays deposited on the cholesteryl-polyether/glass surface with (a & b) or without (c & d) 2% ganglioside GM1. The red channel shows TR-DHPE (0.5%) and the green channel detects the binding of FITC-CTB. Panel (e) is competitive assay of the binding of FITC-CTB to the $GM_1$ containing SLB array from a solution containing 1 nM FITC-CTB and varying concentrations (C/nm) of CTB without dye label.

Our ability to form fluidic and air-stable SLB microarrays from simple robotic spotting has opened the door to large scale screening of cell surface interactions. We demonstrate this using two model systems. In the first system, we incorporate into the SLB 2% ganglioside $GM_1$, a glycolipid containing the oligosaccharide unit for the specific binding by cholera toxin B (CTB) subunits. We choose this model system because the pentameric CTB is known to bind to five $GM_1$ and this multivalent interaction is expected to require fluidity in cluster formation [Biochem. 1989, 28, 5019-5024]. The fluorescence microscopy images in FIG. 7 show SLB arrays with (a & b) or without (c & d) $GM_1$. As expected, the green dye-tagged CTB binds specifically to $GM_1$ containing SLB arrays. We carry out FRAP measurements on SLB spots after CTB binding and find that the TR-DHPE lipids (red channel) remain mobile while the CTB-$GM_1$ complexes (green channel) are not, in agreement with previous studies [J. Am. Chem. Soc. 2005, 127, 2826-2827]. We also carry out quantitative analysis of binding on the SLB microarray using a competition assay. Panel (e) in FIG. 7 shows the amount of surface bound FITC-CTB (green fluorescence intensity) as a function of solution phase CTB (without dye label) in the presence of 1 nM FITC-CTB. The data gives an $IC_{50}$ value of ~6 nM, in agreement with previous measurements on CTB binding to ganglioside $GM_1$ in lipid membranes supported on microspheres [Biochem. 2002, 41, 1742-1751].

Figure 8:
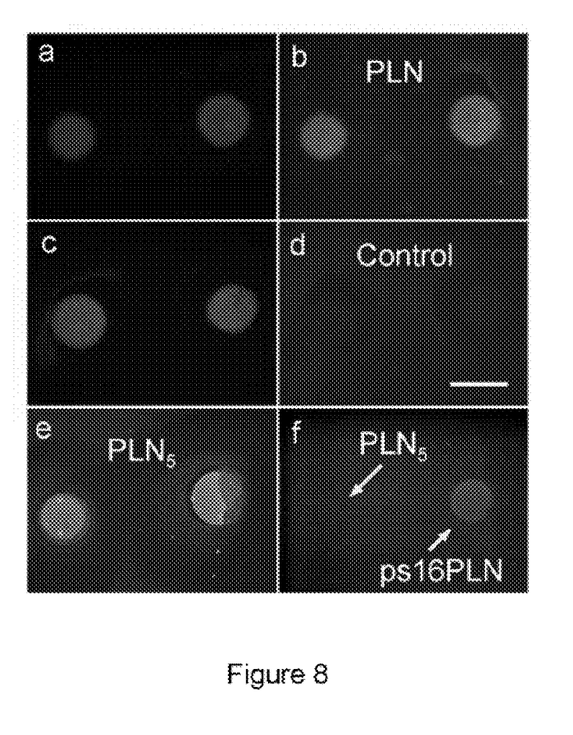
FIG. 8 shows fluorescence microscopic images of SLB arrays deposited on the cholesteryl-polyether/glass surface: (a & b) Spots containing PLN with a protein/lipid ratio of 1:100; (c & d) controls without protein; (e) spots containing PLN$_5$ with a protein cluster/lipid ratio of 1:500, and (f) spots containing PLN$_5$ (left) with a protein cluster/lipid ratio of (1:500) and pS16-PLN (right) with a ratio of (1:100). The red channel is for TR-DHPE and green for FITC-2$^{nd}$ antibody. A primary antibody against PLN is used for (b,d,e) and that specific for pS16-PLN in (f). The scale bar in panel (d) is 400 μm.

In the second model, we use phospholamban (PLN), a single-pass integral membrane protein which inhibits the sarcoplasmic reticulum calcium ATPase (SERCA), thus regulating heart muscle contraction and relaxation. We incorporate both monomeric (PLN, 6 kDa) and pentameric ($PLN_5$, 30 kDa) formed into SLB microarrays and use an antibody (Anti-PLN) against PLN for specific detection. FIG. 8 shows specific detection of PLN. The red channel (TR-DHPE) shows the position of the spots and the green channel is immunostaining (FITC-$2^{nd}$ antibody). The control (c & d) shows spots without protein incorporation. Anti-PLN recognizes $PLN_5$ (e) with higher affinity than that for the monomer (b), indicating the more accessibility of antibody binding sites on $PLN_5$. In addition, we demonstrate that our approach is sensitive to post-translational modifications. In fact, PLN is phosphorylated at S16 by protein kinase A, a process which releases SERCA inhibition and re-establishes calcium flux. We reconstituted phosphorylated PLN at serine 16 (pS16-PLN) in SLB arrays and using anti-pS16-PLN antibody we are able to localize this protein (f).

REFERENCES CITED

US Patent Documents

U.S. Pat. No. 5,922,594, Jul. 13, 1999, Lofangs et al.
U.S. Pat. No. 6,756,078, Jun. 29, 2004, Bookbinder et al.
U.S. Pat. No. 7,045,171, May 16, 2006, Bookbinder et al.
2004/0096914A1, May 20, 2004, Fang et al.
U.S. Pat. No. 5,919,576, Jul. 6, 1999, Hui et al.

OTHER REFERENCES

Brian, A. A.; McConnell, H. M. "Allogenic stimulation of cytoxic T cells by supported planar membrane", PNAS 1984, 81, 6159-6163.
Sackmann, E. "Supported membranes: scientific and practical applications", Science 1996, 271, 43-48.
Groves, J. T.; Boxer, S. G. "Micropattern formation in supported lipid membranes" Acc. Chem. Res. 2002, 35, 149-157.
Tanaka, M.; Sackmann, E. "Polymer-supported membranes as models of the cell surface," Nature 2005, 437, 656-663.
Wagner, M. L.; Tamm, L. K. "Tethered polymer-supported planar lipid bilayers for reconstitution of integral membrane proteins: silane-polyethyleneglycol-lipid as a cushion and covalent linker," Biophys. J. 2000, 1400-1414.
Naumann, C. A.; Prucker, O.; Lehmann, T.; Ruhe, J.; Knoll, W.; Frank, C. W. "The polymer-supported phospholipid bilayer: tethering as a new approach to substrate-membrane stabilization," Biomacromolecules 2002, 3, 27-35.
Plant, A. L. "Supported Hybrid Bilayer Membranes as Rugged Cell Membrane Mimics," Langmuir, 1999, 15, 5128-5135.
Winger, T. M.; Ludovic, P. J.; Chaikof, E. L. "Formation and stability of complex membrane-mimetic monolayers on solid supports," Langmuir 1999, 15, 3866-3874.
Ross, E. E.; Rozanski, L. J.; Spratt, T.; Liu, S.; O'Brien, D. F.; Saavedra, S. S. "Planar Supported Lipid Bilayer Polymers Formed by Vesicle Fusion. 1. Influence of Diene Monomer Structure and Polymerization Method on Film Properties," Langmuir, 2003, 19, 1752-1765.
Holden, M. A.; Jung, S.-Y.; Yang, T.; Castellana, E. T.; Cremer, P. S. "Creating Fluid and Air-Stable Solid Supported Lipid Bilayers," J. Am. Chem. Soc. 2004, 126, 6512-6513.
Albertorio, F.; Diaz, A. J.; Yang, T.; Chapa, V. A.; Kataoka, S.; Castellana, E. T.; Cremer, P. S. "Fluid and Air-Stable Lipopolymer Membranes for Biosensor Applications," Langmuir; 2005, 21, 7476-7482.
Albertorio, F.; Chapa, V. A.; Chen, X.; Diaz, A. J.; Cremer, P. S. "The α,α-(1→1) Linkage of Trehalose is Key to Anhydrobiotic Preservation," J. Am. Chem. Soc. 2007, 129, 10567-10574.
Crowe, J. H.; Crowe, L. M. "Preservation of mammalian cells—learning nature's tricks," Nature Biotech. 2000, 18, 145-146.
Henriksen, J., Rowat, A. C., Brief, E., Hsueh, Y. W., Thewalt, J. L., Zuckermann, M. J., H. Ipsen, J. "Universal Behavior of Membranes with Sterols," Biophys. J. 2006, 90, 1639-1649.
Simons, K.; Vaz, W. L. "Model systems, lipid rafts, and cell membranes," Annu. Rev. Biophys. Biomol. Struct. 2004, 33, 269-295.
Cheng, Y.; Boden, N.; Bushby, R. J.; Clarkson, S.; Evans, S. D.; Knowles, P. F.; Marsh, A.; Miles, R. E. "Attenuated Total Reflection Fourier Transform Infrared Spectroscopic Characterization of Fluid Lipid Bilayers Tethered to Solid Supports," Langmuir 1998, 14, 839-844.
Jeuken, L. J. C.; Daskalakis, N. N.; Han, X.; Sheikh, K.; Erbe, A. Bushby, R. J.; Evans, S. D. "Phase separation in mixed self-assembled monolayers and its effect on biomimetic membranes," Sensors & Actuators B 2007, 124, 501-509.
Knoll, W.; Frank, C. W.; Heibel, C.; Naumann, R.; Offenhausser, A.; Ruhe, J.; Schmidt, E. K.; Shen, W. W.; Sinner, A. "Functional tethered lipid bilayers," Rev. Mol. Biotech. 2000, 74, 137-158.
Carman, C. V.; Springer, T. A. "Integrin avidity regulation: are changes in affinity and conformation underemphasized?" Curr. Opin. Cell. Biol. 2003, 15, 547-556
S. J. Singer, "Intercellular communication and cell-cell adhesion," Science 1992, 255, 1671-1677.
Grakoui, A.; Bromley, S. K.; Sumen, C.; Davis, M. M.; Shaw, A. S.; Allen, P. M.; Dustin, M. L. "The immunological synapse: a molecular machine controlling T cell activation," Science, 1999, 285, 221-227.
Cha, T.-W.; Guo, A.; Zhu, X.-Y. "Enzymatic activity on a chip: the critical role of protein orientation," Proteomics, 2005, 5, 416-419
Buck, B., Zamoon, J., Kirby, T. L., DeSilva, T. M., Karim, C., Thomas, D.; Veglia, G. "Overexpression, purification and characterization of recombinant Ca-ATPase regulators for high-resolution solution and solid-state NMR studies," Protein Expr. Purif. 2003, 30, 253-261.

Metcalfe, E. E.; Traaseth, N. J.; Veglia, G. "Serine 16 Phosphorylation Induced an Order-to-Disorder Transition in Monomeric Phospholamban," Biochem. 2005, 44, 4386-4396.

Traaseth, N. J.; Buffy, J. J, Zamoon, J., Veglia G. "Structural Dynamics and Topology of Phospholamban in Oriented Lipid Bilayers Using Multi-dimensional Solid-State NMR," Biochem. 2006, 45, 13827-13834.

Schon, A.; Freire, E. "Thermodynamics of intersubunit interactions in cholera toxin upon binding to the oligosaccharide portion of its cell surface receptor, ganglioside GM1," Biochem. 1989, 28, 5019-5024.

Yamazaki, V.; Sirenko, O.; Schafer, R. J.; Groves, J. T. "Lipid Mobility and Molecular Binding in Fluid Lipid Membranes," J. Am. Chem. Soc. 2005, 127, 2826-2827.

Lauer, S.; Goldstein, B.; Nolan, R. L.; Nolan, J. P. "Analysis of Cholera Toxin-Ganglioside Interactions by Flow Cytometry," Biochem. 2002, 41, 1742-1751.

Cremer, P. S.; Boxer, S. G. "Formation and Spreading of Lipid Bilayers on Glass Surfaces," J. Phys. Chem. B 1999, 103, 2554-2559.

McBee, T. W.; Saavedra, S. S. "Stability of Lipid Films Formed on □-Aminopropyl Monolayers," Langmuir 2005, 21, 3396-3399.

Fang, Y., Frutos, A. G.; Lahiri J. "Membrane protein microarrays," J. Am. Chem. Soc. 2002, 124, 2394-2395.

Axelrod, D.; Koppel, D. E.; Schlessinger, J.; Elson, E.; Webb, W. W. "Mobility measurement by analysis of fluorescence photobleaching recovery kinetics," Biophys. J. 1976, 16, 1055-1069.

The invention claimed is:

1. A method of producing a supported lipid bilayer membrane via the following steps (i) providing a solid substrate surface; (ii) covalent attachment of a density between $1 \times 10^{12}/cm^2$ and $1 \times 10^{14}/cm^2$ of sterol groups to the solid substrate surface; (iii) and contacting the sterol functionalized solid substrate surface with a lipid solution to form a supported lipid bilayer membrane, wherein the resulting supported lipid bilayer membrane possesses air-stability and the said air-stability means that the supported lipid bilayer membrane remains intact on the substrate surface after the substrate has been removed from an aqueous solution, exposed to the ambient air at room temperature, and re-immersed in the aqueous solution.

2. The method of claim 1, wherein the said sterol is cholesterol or chemically modified cholesterol.

3. The method of claim 1, wherein the said density of the sterol groups covalently attached to the solid substrate surface is between $1 \times 10^{13}/cm^2$ and $10^{14}/cm^2$.

4. The method of claim 1, wherein the solid substrate surface is coated with an immobilized molecular film.

5. The method of claim 4, wherein the said molecular film is a hydrophilic polymer cushion, an immobile monolayer, or a hydrogel coating.

6. The method of claim 5, wherein the said hydrophilic polymer is a polyether, a poly (ethylene glycol), a multi-armed poly (ethylene glycol), a star-shaped poly (ethylene glycol), a hyperbranched polyglycidol, a polyacrymide, or a polylysine.

7. The method of claim 4, wherein the said molecular film is functionalized to present $—CO_2^-$, $—PO_4^{2-}$, or $—NH_3^+$ charge groups.

8. The method of claim 1, wherein the said solid substrate is a glass surface, a silica surface, a quartz surface, a silicon surface, a metal surface, a metal oxide surface, a ceramic surface, a semiconductor surface, a plastic surface, or a polymer surface.

9. The method of claim 1, wherein the said sterol groups are attached to the solid substrate surface via molecular tethers.

10. The method of claim 1, wherein the said solid substrate surface is coated with polyethers terminated with —OH groups, and the said attachment of sterol groups involves ester bonds.

11. The method of claim 1, wherein the said lipid solution contains lipid vesicles or liposomes.

12. The method of claim 1, wherein the said lipid solution contains membrane proteins or peptides.

13. The method of claim 1, wherein the said lipid solution contains glycol lipids.

14. The method of claim 1, wherein the said contacting step is carried out in an array format to form a supported lipid bilayer membrane microarray.

15. A method of producing an air-stable supported lipid bilayer membrane via the following steps: (i) covalently attaching sterol groups to one end of a molecular tether with a functional group "A" at the opposite end; (ii) mixing the tethered sterol with a lipid solution to give a mixed lipid solution; (iii) providing a solid substrate surface presenting a density between $1 \times 10^{12}/cm^2$ and $1 \times 10^{14}/cm^2$ of functional group "B" which is reactive towards "A" for covalent bond formation; and (iv) contacting the said mixed lipid solution from step (ii) with the said solid substrate surface from step (iii) to form the air-stable supported lipid bilayer membrane, wherein the said air-stable supported lipid bilayer membrane means that the supported lipid bilayer membrane remains intact on the substrate surface after the substrate has been removed from an aqueous solution, exposed to the ambient air at room temperature, and re-immersed in the aqueous solution.

16. The method of claim 15, wherein the said density is between $1 \times 10^{13}/cm^2$ and $1 \times 10^{14}/cm^2$.

17. The method of claim 15, wherein the said molecular tether in step (i) is an oligo-(ethyleneglycol), the said functional group "A" is an $—NH_2$ group, and the said functional group "B" in step (iii) is an N-hydroxysuccinimide ester, an epoxy group, or an aldehyde group.

18. The method of claim 15, wherein the said solid substrate surface is coated with an immobilized molecular film.

19. The method of claim 18, wherein the said molecular film is a polymer coating, an immobile monolayer, or a hydrogel.

20. The method of claim 19, wherein the said polymer is a polyether.

21. The method of claim 20, wherein the said polyether is a poly (ethylene glycol), a multi-armed poly (ethylene glycol), a star-shaped poly (ethylene glycol), a hyperbranched polyglycidol, a polyacrymide, or a polylysine.

22. The method of claim 15, wherein the said solid substrate is a glass surface, a silica surface, a quartz surface, a silicon surface, a metal surface, a metal oxide surface, a semiconductor surface, a ceramic surface, a plastic surface, or a polymer surface.

23. The method of claim 15, wherein the said lipid solution contains lipid vesicles or liposomes.

24. The method of claim 15, wherein the said lipid solution contains membrane proteins or peptides.

25. The method of claim 15, wherein the said lipid solution contains glycol lipids.

26. The method of claim 15, wherein the said contacting step (iv) is carried out in an array format to form a supported lipid bilayer membrane microarray.

27. A supported lipid bilayer membrane or supported lipid bilayer membrane microarray on a solid surface, wherein the said supported lipid bilayer membrane possesses air-stability and contains mobile lipid molecules in the form of lipid bilayer and a density between $1\times10^{12}/cm^2$ and $1\times10^{14}/cm^2$ of sterol groups covalently linked to the said solid surface; wherein the said air-stability means that the supported lipid bilayer membrane remains intact on the substrate surface after the substrate has been removed from an aqueous solution, exposed to the ambient air at room temperature, and re-immersed in the aqueous solution.

28. The lipid bilayer membrane or lipid bilayer membrane microarray of claim 27, wherein the said solid surface is a glass surface, a silica surface, a quartz surface, a silicon surface, a metal surface, a metal oxide surface, a semiconductor surface, a ceramic surface, a plastic surface, or a polymer surface.

29. The lipid bilayer membrane or lipid bilayer membrane microarray of claim 27, wherein the said solid surface is coated with a polymer cushion.

30. The lipid bilayer membrane or lipid bilayer membrane microarray of claim 27, wherein the said solid surface is coated with an immobilized molecular film.

31. The lipid bilayer membrane or lipid bilayer membrane microarray of claim 27, wherein the said solid surface is coated with a hydrogel.

32. The lipid bilayer membrane or lipid bilayer membrane microarray of claim 27, wherein the said lipid bilayer membrane contains membrane proteins or peptides.

33. The lipid bilayer membrane or lipid bilayer membrane microarray of claim 27, wherein the said lipid bilayer membrane contains glycolipids.

34. The lipid bilayer membrane or lipid bilayer membrane microarray claim 27, wherein the said density is between $1\times10^{13}/cm^2$ and $1\times10^{14}/cm^2$.

* * * * *